(12) United States Patent
Seim

(10) Patent No.: US 6,658,286 B2
(45) Date of Patent: Dec. 2, 2003

(54) ATRIAL AND VENTRICULAR TACHYARRHYTHMIA DETECTION SYSTEM AND METHOD

(75) Inventor: Gary Seim, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 298 days.

(21) Appl. No.: 09/827,769

(22) Filed: Apr. 6, 2001

(65) Prior Publication Data
US 2002/0147407 A1 Oct. 10, 2002

(51) Int. Cl.[7] .............................. A61B 5/0464
(52) U.S. Cl. .................. 600/516; 600/518; 607/14
(58) Field of Search ............................ 600/515, 518, 600/519, 516; 607/14, 5, 4

(56) References Cited

U.S. PATENT DOCUMENTS

| | | | | |
|---|---|---|---|---|
| 5,205,283 A | * | 4/1993 | Olson | 607/4 |
| 5,379,776 A | * | 1/1995 | Murphy et al. | 600/518 |
| 5,776,072 A | * | 7/1998 | Hsu et al. | 600/518 |
| 5,978,707 A | * | 11/1999 | Krig et al. | 607/14 |

* cited by examiner

Primary Examiner—Kennedy Schaetzle
(74) Attorney, Agent, or Firm—Crawford Maunu PLLC

(57) ABSTRACT

Detecting atrial and ventricular tachyarrhythmias involves classifying atrial interval rates in an atrial window having a first length and ventricular interval rates in a ventricular window having a second length. The second length of the ventricular window differs from the first length of the atrial window to enhance detection of ventricular arrhythmias relative to atrial arrhythmia detection. The atrial and ventricular interval rates in the respective windows are classified as fast or acceptable with respect to predefined thresholds. A ventricular episode is declared in response to satisfying the ventricular window according to a second satisfaction criterion. An atrial episode is declared in response to satisfying the atrial window according to a first satisfaction criterion.

48 Claims, 9 Drawing Sheets

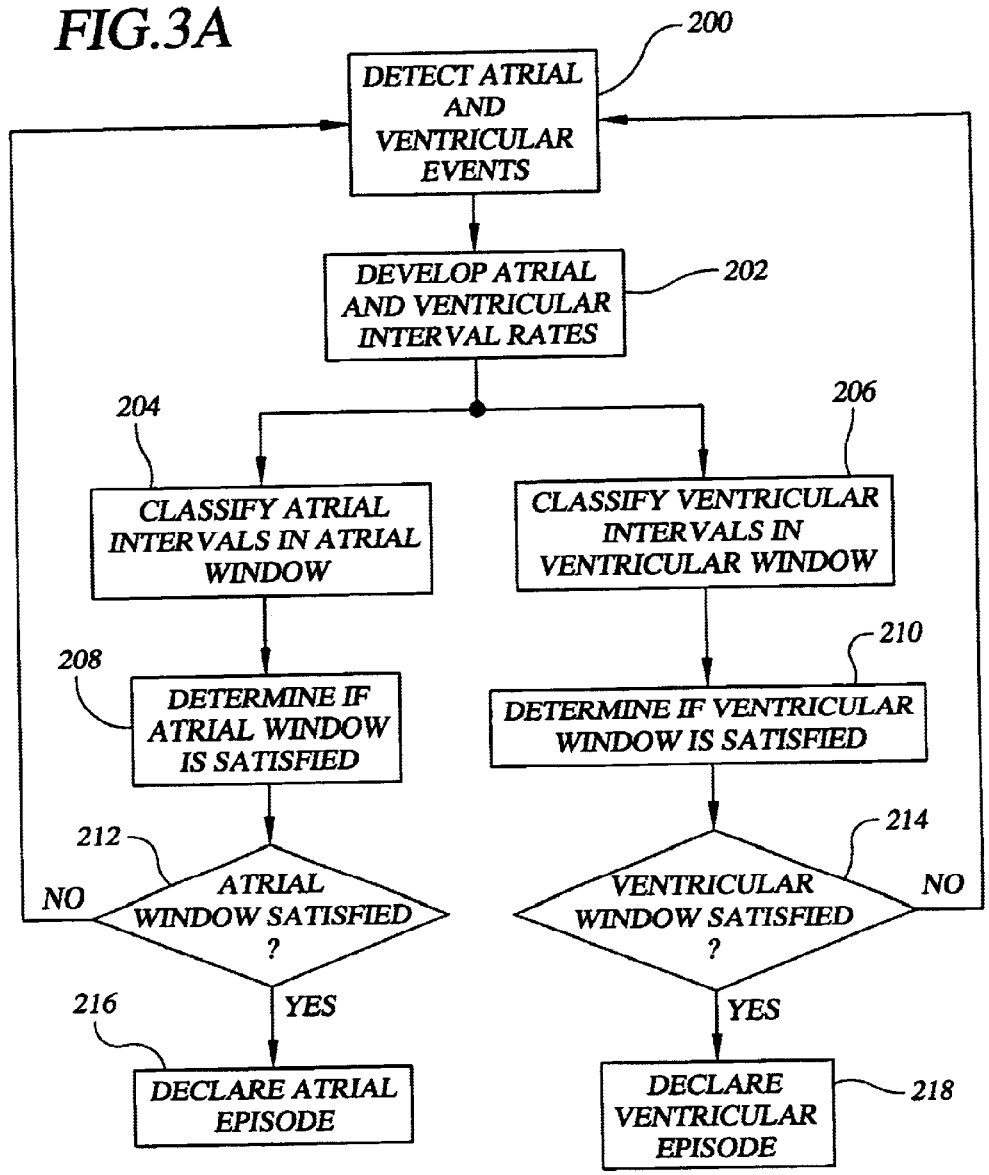

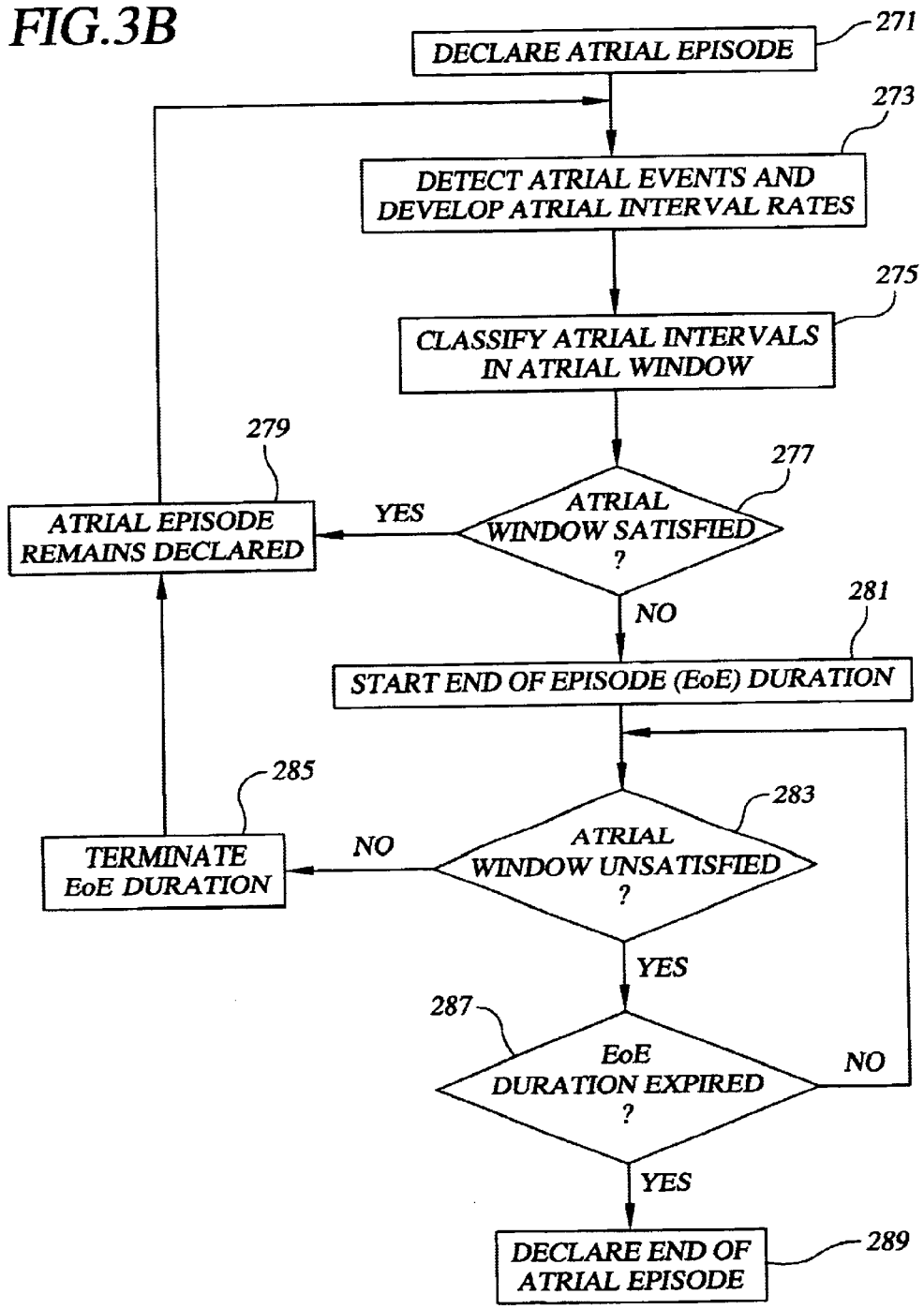

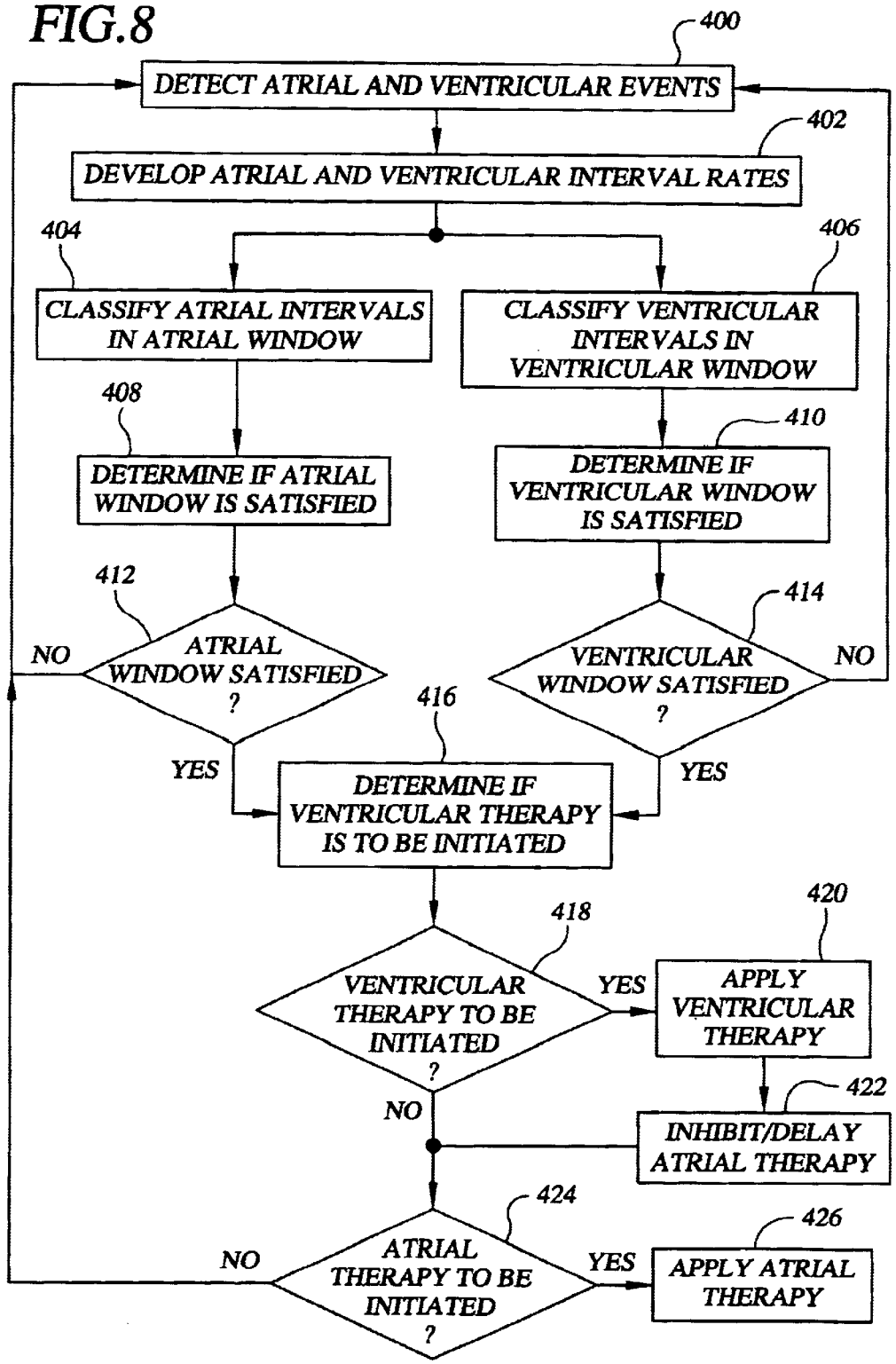

ATRIAL AND VENTRICULAR TACHYARRHYTHMIA DETECTION SYSTEM AND METHOD

FIELD OF THE INVENTION

The present invention relates generally to implantable medical devices and, more particularly, to implantable pacemakers and cardioverter-defibrillators for detecting and treating atrial and ventricular tachyarrhythmias.

BACKGROUND OF THE INVENTION

Implantable cardioverter-defibrillators (ICDs) have been developed that employ detection algorithms capable of recognizing and treating ventricular tachycardias and ventricular fibrillation. Detection algorithms are also being developed to recognize and treat atrial tachycardias and atrial fibrillation. In general, ICDs are designed to treat such tachycardias with antitachycardia pacing and low-energy cardioversion shocks in conjunction with back-up defibrillation therapy. These ICDs monitor the heart rate and the onset of the arrhythmia by sensing endocardial signals and determining when the heart is in need of either cardioversion to treat a given tachycardia or of defibrillation to treat a fibrillation condition.

Certain ICDs have been designed with dual chamber sensing capabilities to detect and analyze both ventricular and atrial endocardial signals. This increase in cardiac signal input to the ICD has provided an opportunity to determine the origin and the nature of atrial and ventricular tachyarrhythmia, and to reduce the frequency of inappropriate therapy being delivered to an implant patient.

However, while the combination of antitachycardia pacing with low and high energy shock delivery, as well as backup bradycardia pacing, in ICDs has expanded the number of clinical situations in which the device may appropriately be employed, improved means of coordinating ventricular and atrial rate information in a way that results in a system that effectively and efficiently treats ventricular and atrial tachyarrhythmias is still desired.

For the reasons stated above, and for other reasons stated below which will become apparent to those skilled in the art upon reading the present specification, there is a need in the art for improved atrial and ventricular arrhythmia detection techniques. There exists a further need for such techniques that provide for preferential detection and treatment of ventricular arrhythmias relative to atrial arrhythmias. The present invention fulfills these and other needs.

SUMMARY OF THE INVENTION

The present invention is directed to systems and methods for detecting arrhythmias. One embodiment of the present invention provides for improved atrial tachyarrhythmia detection. Another embodiment of the present invention provides for improved atrial and ventricular tachyarrhythmia detection. In an embodiment which provides for concurrent detection of atrial and ventricular tachyarrhythmia, the detection methodology provides for increased sensitivity and response to ventricular tachyarrhythmia detection relative to atrial tachyarrhythmia detection and response sensitivity.

An arrhythmia detection methodology of the present invention is preferably implemented with an implantable medical device, such as devices that provide for one or a combination of pacing, cardioverting, defibrillating, and re-synchronizing functions. According to one embodiment, atrial and ventricular interval rates are developed from sensed atrial and ventricular events, respectively. Atrial interval rates are classified in an atrial window. The atrial window is defined to have a first length and a first satisfaction criterion. The atrial interval rates in the atrial window are typically classified as fast or slow with respect to a predefined threshold.

Ventricular interval rates are classified in a ventricular window. The ventricular window is defined to have a second length and a second satisfaction criterion. The second length of the ventricular window differs from the first length of the atrial window so as to enhance detection of ventricular arrhythmias relative to atrial arrhythmia detection. The ventricular interval rates in the ventricular window are typically classified as fast or slow.

A ventricular episode is declared in response to satisfying the ventricular window by comparing classified ventricular interval rates to the second satisfaction criterion. An atrial episode is declared in response to satisfying the atrial window by comparing classified atrial interval rates to the first satisfaction criterion. One or more additional detection or verification operations may be performed to verify continuance of a sustained, rather than transitory, ventricular arrhythmia condition. One or more additional detection or verification operations may be performed to verify continuance of a sustained, rather than transitory, atrial arrhythmia condition.

In one embodiment, a plurality of atrial and ventricular windows are operative with respect to each of a plurality of rate zones. In such a configuration, each of the developing, classifying, and declaring processes are operative with respect to each of the plurality of rate zones.

In accordance with another embodiment of the present invention, atrial and ventricular interval rates are developed from sensed atrial and ventricular events, respectively. An atrial window having a first length and a first satisfaction criterion is provided. A ventricular window having a second length and a second satisfaction criterion is also provided. The second length of the ventricular window differs from the first length of the atrial window to enhance detection of ventricular arrhythmias relative to atrial arrhythmia detection. Operations are performed to determine if the atrial and ventricular windows are satisfied according to the first and second satisfaction criteria, respectively.

The detection methodology according to this embodiment provides for determining, in response to satisfaction of the ventricular window, whether ventricular arrhythmia therapy is to be initiated. The detection methodology further provides for determining, in response to satisfaction of the atrial window and non-initiation of ventricular arrhythmia therapy, whether atrial arrhythmia therapy is to be initiated.

Atrial arrhythmia therapy is inhibited or delayed under several scenarios. Atrial arrhythmia therapy is inhibited or delayed during a time period in which initiation of ventricular arrhythmia therapy is being determined. Inhibiting or delaying the atrial arrhythmia therapy also occurs if the atrial and ventricular interval rates are substantially equal. Atrial arrhythmia therapy is inhibited or delayed if an average of the ventricular interval rates is greater than an average of the atrial interval rates. Inhibiting or delaying atrial arrhythmia therapy is also effected if a representative atrial rate developed from the atrial interval rates fails to exceed a representative ventricular rate developed from the ventricular interval rates by at least a predetermined factor. For example, atrial arrhythmia therapy is inhibited or delayed if an average or median of the atrial interval rates fails to exceed an average or median of the ventricular interval rates by at least a predetermined factor.

In accordance with yet another embodiment of the present invention, a body implantable system for detecting atrial and/or ventricular arrhythmia includes at least one lead comprising atrial and ventricular electrodes. A detector is coupled to the lead, and senses atrial events and ventricular events. Memory is configured to define an atrial window having a first length and a first satisfaction criterion. The memory is also configured to define a ventricular window having a second length and a second satisfaction criterion. The second length of the ventricular window differs from the first length of the atrial window to enhance detection of ventricular arrhythmias relative to atrial arrhythmia detection.

A control circuit is coupled to the detector and memory. The control circuit classifies atrial and ventricular interval rates in the atrial and ventricular windows, respectively. The control circuit declares a ventricular episode in response to satisfying the ventricular window by comparing classified ventricular interval rates to the second satisfaction criterion. The control circuit also declares an atrial episode in response to satisfying the atrial window by comparing classified atrial interval rates to the first satisfaction criterion. The control circuit inhibits atrial arrhythmia therapy under several scenarios, such as those discussed hereinabove.

In accordance with systems and methods of the present invention, the first length of the atrial window is greater than the second length of the ventricular window. For example, the first length of the atrial window length may be between two times and four times the second length of the ventricular window. By way of further example, the first length of the atrial window may be at least four times greater than the second length of the ventricular window.

The first satisfaction criterion associated with the atrial window is typically different from the second satisfaction criterion associated with the ventricular window. Alternatively, the first and second satisfaction criteria may be the same. Each of the first and second satisfaction criterion may represent a predetermined number, a predetermined percentage or a predetermined ratio of the classified atrial and ventricular interval rates relative to the first and second lengths. For example, the first satisfaction criterion may represent a predetermined number, percentage or ratio of the atrial interval rates classified as fast atrial interval rates relative to the first length. The second satisfaction criterion, in this case, represents a predetermined number or percentage of the ventricular interval rates classified as fast ventricular interval rates relative to the second length.

By way of particular example, the first satisfaction criterion may represent 32 of 40 (or 80 percent) of the atrial interval rates classified as fast atrial interval rates in the atrial detection window. The second satisfaction criterion, according to this example, may also represent 8 of 10 (or 80 percent) of the ventricular interval rates classified as fast ventricular interval rates in the ventricular detection window.

According to another embodiment, an atrial episode is verified as being a sustained atrial episode in response to satisfaction of the atrial window by a third satisfaction criterion for subsequent atrial interval rates. Each of the first and third satisfaction criterion may, for example, represent a predetermined number, percentage or ratio of the atrial interval rates classified as fast atrial interval rates relative to the first length, and the third satisfaction criterion is less than the first satisfaction criterion. The first satisfaction criterion, according to one approach, represents about 80 percent of the atrial interval rates classified as fast atrial interval rates and the third satisfaction criterion represents about 60 percent of the subsequent atrial interval rates classified as fast atrial interval rates.

A ventricular episode, according to this embodiment, is verified as being a sustained ventricular episode in response to the ventricular window being satisfied by a fourth satisfaction criterion for subsequent ventricular interval rates. Each of the second and fourth satisfaction criterion represents a predetermined number, percentage or ratio of the ventricular interval rates classified as fast ventricular interval rates relative to the second length, and the fourth satisfaction criterion is less than the second satisfaction criterion. For example, the second satisfaction criterion may represent about 80 percent of the ventricular interval rates classified as fast ventricular interval rates and the fourth satisfaction criterion may represent about 60 percent of the subsequent ventricular interval rates classified as fast ventricular interval rates.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 3A is a flow chart depicting various processes of an atrial and ventricular arrhythmia detection methodology associated with declaring atrial and ventricular episodes in accordance with an embodiment of the present invention;

FIG. 3B is a flow chart depicting various processes of an atrial and ventricular arrhythmia detection methodology associated with ending an atrial episode in accordance with an embodiment of the present invention;

FIG. 8 is a flow chart depicting various processes of an atrial and ventricular arrhythmia detection methodology in accordance with yet another embodiment of the present invention.

Figure 1:
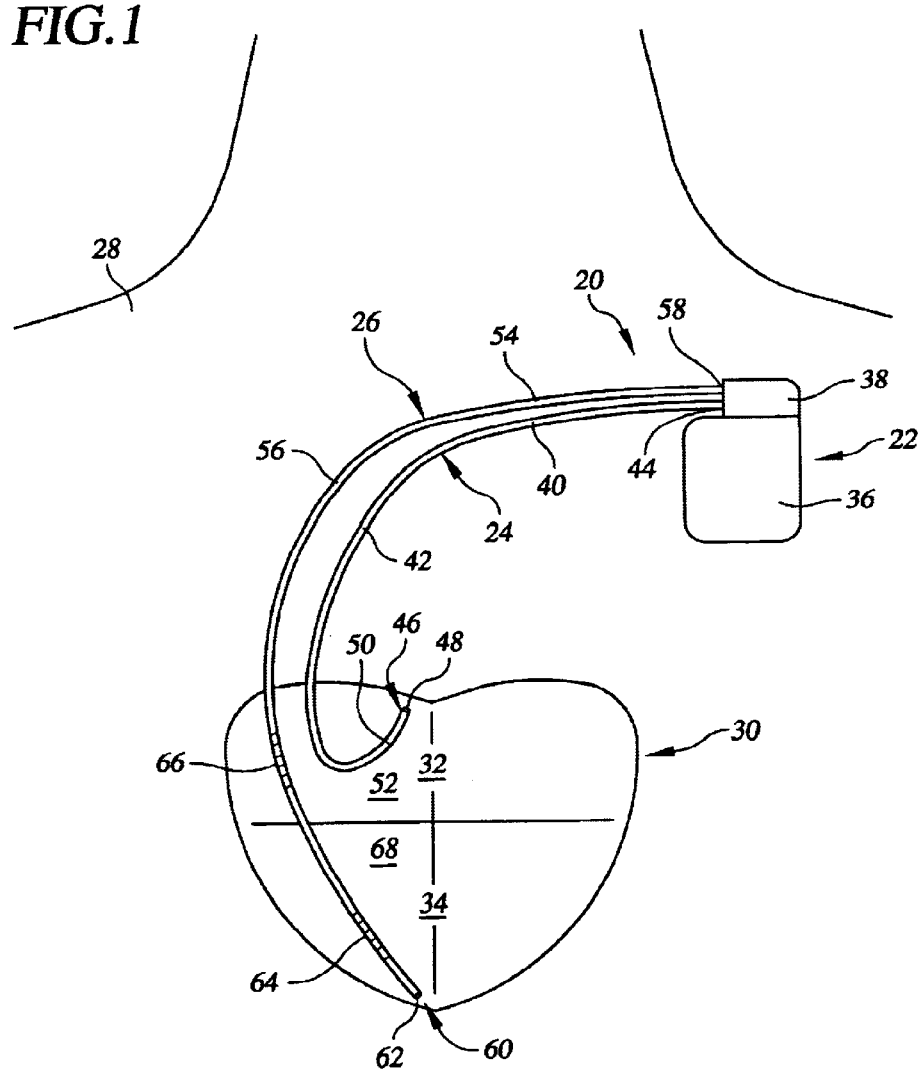
FIG. 1 is a depiction of an implantable medical device with which the atrial and ventricular arrhythmia detection methodologies of the present invention may be practiced.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Referring now to the figures, and more particularly to FIG. 1, there is shown a is body implantable system 20 that represents one of several types of systems with which arrhythmia detection methodologies of the present invention may be practiced. For example, the implantable pulse generator 22 may be representative of all or part of a pacemaker, defibrillator, cardioverter, cardiac monitor, or re-synchronization device. Accordingly, the arrhythmia detection methodologies of the present invention may be practiced in a wide variety of implantable medical devices that sense cardiac activity.

The body implantable system 20 is shown to include an implantable pulse generator 22 coupled to an atrial lead 24 and a ventricular lead 26. The system 20 may also include endocardial pacing and cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at a desired site.

The system 20, as shown in FIG. 1, is implanted in a human body 28 with portions of the atrial and ventricular leads 24 and 26 inserted into a heart 30 to detect and analyze electric cardiac signals produced by both the atria 32 and the ventricles 34 of the heart 30. The atrial and ventricular leads 24 and 26 also provide electrical energy to the heart 30 under certain predetermined conditions to treat various types of cardiac arrhythmia, including, for example, atrial and ventricular tachycardias, and atrial and ventricular fibrillation of the heart 30.

Figure 2:
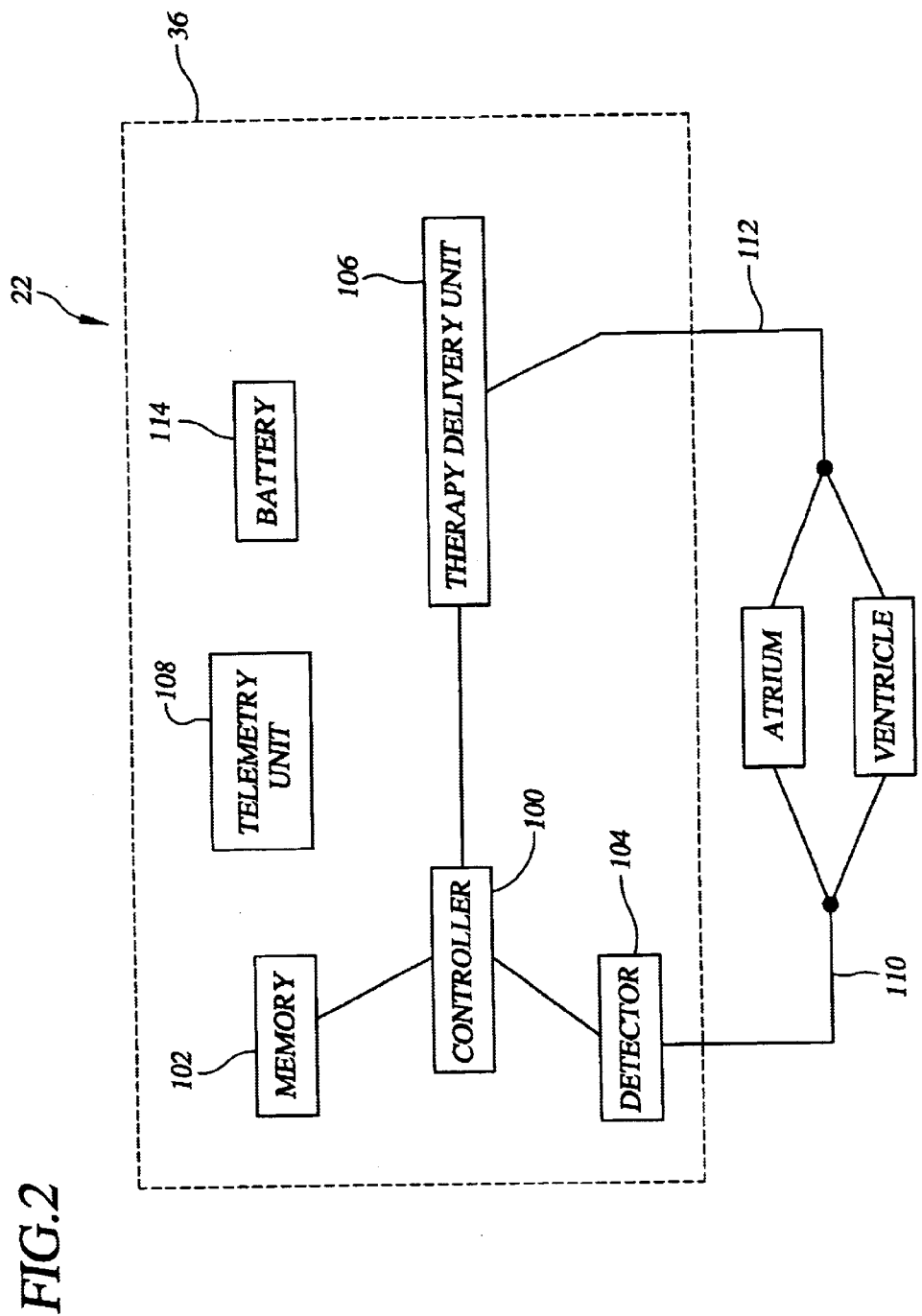
FIG. 2 is a block diagram of several components housed in the implantable medical device of FIG. 1.

A block diagram of the implantable pulse generator 22 electronics is provided in FIG. 2. The implantable pulse generator 22 includes a housing 36 which contains, among other components, a controller 100 and memory 102, which typically includes read only memory (ROM) and random access memory (RAM). Pulse generator 22 further includes a detector 104, which includes atrial and ventricular sense amplifiers (not shown), a therapy delivery unit 106, and a telemetry unit 108. The electronic components of the pulse generator 22 are interconnected by way of a bus connection (not shown).

Power to the implantable pulse generator 22 is supplied by an electrochemical battery 114 which is contained within the implantable pulse generator housing 36. The implantable pulse generator 22 is interrogated and programmed via bidirectional radio frequency telemetry through cooperative operation between the telemetry unit 108 and an external programmer in a manner known in the art.

The arrhythmia detection methodologies implemented by system 20 are embodied in one or more algorithms as firmware within memory 102, and are executed by the controller 100. The detector 104 is also connected to the controller 100, and contains a plurality of electrical connections 110 coupled to the atrial and ventricular sense amplifiers. The outputs of the sense amplifiers are connected to the controller 100, such that atrial and ventricular signals received through the detector 104 are analyzed by the algorithms implemented within the controller 100. The controller 100 is also coupled to the therapy delivery unit 106, which controls the delivery of electrical energy to the heart 30 through a plurality of electrical output connections 112 to affect the sinus rhythm of the heart 30 under certain combinations of atrial 32 and ventricular 34 conditions.

Referring again to FIG. 1, a connector block 38 is mounted on the implantable pulse generator 22. The connector block 38 has two connector ports for coupling the atrial lead 24 and the ventricular lead 26 to the detector 104 and the therapy delivery unit 106 of the implantable pulse generator 22. Additional connector ports can be added to the connector block 38, as in the case of configurations having three or more ports as is known in the art. Alternatively, the connector block 38 can be provided with one connector port for coupling an implantable transvenous lead to the implantable pulse generator 22. It is understood that atrial and ventricular sensing and pacing/defibrillating functions may be accomplished using a single lead system employing atrial and ventricular conductors/electrodes, rather than by use of the dual lead system shown in FIG. 1.

In general, the electrical activity in the heart 30 is sensed, and therapies are delivered to the heart 30, through at least one transvenous pacing/defibrillation lead connected to the implantable pulse generator 22. Unipolar and/or bipolar pacing and sensing electrodes can be used in conjunction with the transvenous pacing/defibrillation lead. In the embodiment shown in FIG. 1, bipolar leads and sensing circuits are utilized for sensing both the atrial 32 and the ventricular 34 activity. Sensing atrial activity includes the determination of atrial P-waves for purposes of determining atrial intervals. Ventricular activity is monitored by sensing for the occurrence of ventricular R-waves for purposes of determining ventricular intervals. Pacing therapies to the atrium 32 or ventricle 34 are delivered to the heart 30 using these same leads.

The system 20 may also employ defibrillation electrodes which are connected to the electrical output connections 112, and serve to deliver cardioversion and defibrillation level electrical pulses to the heart 30 as determined by the programming of controller 100. The housing 36 of the system 20 may be used as an optional defibrillation electrode, where the housing 36 of the implantable pulse generator 22 is electrically connected to a cathode pole of the therapy delivery unit 106. All defibrillation electrical pulses are delivered to the heart with at least two defibrillation electrodes, or through at least one defibrillation electrode and the housing 36 of the implantable pulse generator 22. The system 20 supports a plurality of pacing regimens.

In addition to the lead configuration shown in FIG. 1, the system 20 supports several other lead configurations and types. For example, it is possible to use ventricular epicardial rate sensing, atrial endocardial bipolar pace/sensing, ventricular endocardial bipolar pace/sensing, epicardial patches, and ancillary leads in conjunction with the implantable pulse generator 22.

In the embodiment of system 20 depicted in FIG. 1, the atrial lead 24 has an elongated body 40 having a peripheral surface 42, proximal and distal ends, 44 and 46, a first atrial electrode 48, and a second atrial electrode 50 on the peripheral surface 42. The first atrial electrode 48 and the second atrial electrode 50 receive bipolar electrical cardiac signals from the right atrium chamber 52 of the heart 30, and are attached on the peripheral surface 42 of the elongated body 40.

The first atrial electrode 48 is situated at or adjacent to the distal end 46 of the elongated body 40 and is either a pacing tip electrode or a semi-annular or annular electrode partially or completely encircling the peripheral surface 42 of the elongated body 40. The second electrode 50 is an annular or semi-annular electrode encircling or partially encircling the peripheral surface 42 of the elongated body 40. The second electrode 50 is spaced longitudinally along the peripheral surface 40 from the first atrial electrode 48 and the distal end 46 of the atrial lead 24, such that when the atrial lead is inserted into the right atrial chamber 52 of the heart 30, the first atrial electrode 48 is in physical contact with a portion of a wall of the right atrial chamber 52 of the heart and the second electrode 50 is within the right atrium chamber 52.

Electrical conductors extend longitudinally within the elongated body 40 of the atrial lead 24 from a connection end at the proximal end 44 and make connection to the first and second atrial electrodes 48 and 50. The proximal end 44 of the atrial pacing lead 24 is attached to the connector block 38 of the implantable pulse generator 22. The connector block 38 provides electrical coupling between the contact ends of the electrical conductors of atrial lead 24 with the atrial sense amplifier of the detector 104 and the therapy delivery unit 106, such that the implantable pulse generator 22 receives bipolar signals from, and delivers bipolar pacing to, the right atrium 52 of the heart 30.

The ventricular lead 26 includes an elongated body 54 having a peripheral surface 56, proximal and distal ends, 58 and 60, and a ventricle pacing electrode 62. The ventricular lead 26 also includes a first defibrillation electrode 64 and a second defibrillation electrode 66 situated on the peripheral surface 56 of the elongated body 54. The ventricular pacing electrode 62 and the first defibrillation electrode 64 are adapted to receive electrical cardiac signals from the right ventricle chamber 68 of the heart 30, and are attached on the peripheral surface of the elongated body 54. The second defibrillation electrode 66 is spaced apart and longitudinally on the peripheral surface 56 of the ventricular lead 26. This configuration affords positioning of the ventricular lead 26 in the heart 30 with the ventricular pacing electrode 62 in the apex of the right ventricle 68, the first defibrillation electrode 64 within the right ventricle chamber of the heart, and the second defibrillation electrode 66 within the right atrium chamber 52 or a major vein leading to right atrium.

Electrical leads extend longitudinally within the elongated body 54 of the ventricular lead 26 from a connection end at the proximal end 58 to make connection with the ventricular pacing electrode 62, the first defibrillation electrode 64, and the second defibrillation electrode 66. The proximal end 58 of the ventricular lead 26 is attached to the connector block 38 of the implantable pulse generator 22. The connector block 38 provides for electrical coupling between the contact ends of the electrical conductors of ventricular lead 26 with the ventricular sense amplifier of the detector 104 and the therapy delivery unit 106, such that the implantable pulse generator 22 receives either unipolar or bipolar signals from, and can deliver unipolar or bipolar pacing to, the right ventricle 68 and defibrillation electrical pulses to the ventricles 34 of the heart 30.

The atrial lead 24 and the ventricular lead 26 are releasably attached to, and are separated from, the implantable pulse generator 22 to facilitate insertion of the atrial lead 24 into the heart 30. The proximal end 44 of the atrial lead 24 and the proximal end 58 of the ventricular lead 26 are adapted to seal together with the connector ports of the implantable pulse generator 22 to thereby engage the contact ends of the atrial lead 24 and the ventricular lead 26 with the plurality of electrical connections 110 and the therapy delivery unit 106 of the implantable pulse generator 22. The implantable pulse generator 22 of the system 20 is then positioned subcutaneously within the body 26.

Referring now to FIG. 3A, there is shown in flow diagram form several processes of an arrhythmia detection methodology associated with declaring atrial and ventricular episodes implemented by system 20 in accordance with an embodiment of the present invention. Detection and response decisions made by the system 20 are based on detected cardiac events and computed event intervals. As is shown in FIG. 3A, atrial and ventricular events are detected 200, from which atrial and ventricular interval rates are developed 202.

Detection of atrial events typically involves sensing of atrial P-waves. An atrial interval rate (e.g., a A—A wave time interval) is computed using the detected atrial P-waves. An average atrial interval rate may also be computed. In a similar manner, detection of ventricular events typically involves sensing of ventricular R-waves. A ventricular interval rate (e.g., a R—R wave time interval) is computed using the detected ventricular R-waves. An average ventricular interval rate may also be computed.

An arrhythmia detection methodology of the present invention advantageously employs two detection windows for analyzing atrial and ventricular rhythms. In particular, an atrial detection window is employed to classify 204 atrial intervals and a ventricular detection window is employed to classify 206 ventricular intervals. The detection parameters of the atrial and ventricular windows are selected to provide for the detection of atrial and ventricular arrhythmias. In particular, the detection parameters of the two windows provide for preferential detection and response to ventricular arrhythmia episodes relative to detection and response to atrial arrhythmia episodes.

Figure 6:
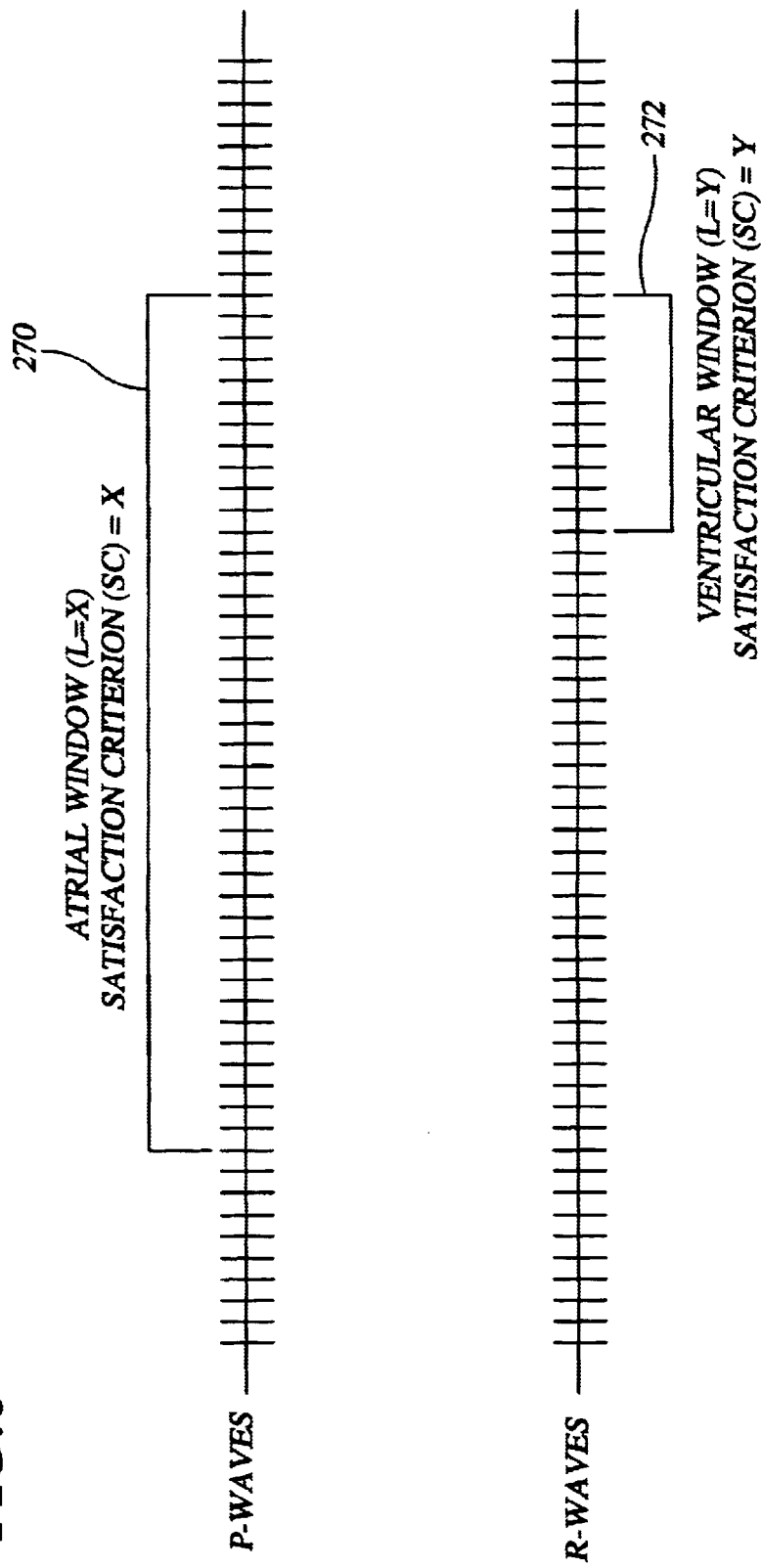
FIG. 6 is an illustration of atrial and ventricular detection windows having differing lengths in accordance with an embodiment of the present invention.

FIG. 6 is an illustration of atrial and ventricular detection windows 270 and 272 having differing detection parameters. According to this embodiment, the atrial window 270 has a length of L=X samples, while the ventricular window 272 has a length of L=Y samples, where X and Y are different numbers. In one particular configuration, the atrial window 270 has a length of L=40, and the ventricular window 272 has a length of L=10. The lengths, L, of the atrial and ventricular windows 270, 272 may, of course be varied. For example, the atrial window 270 may have a length, L, ranging between and 60. The ventricular window 272 may, for example, have a length, L, ranging between 5 and 15.

Each of the atrial and ventricular windows 270, 272 has an associated satisfaction criterion, SC. The satisfaction criteria of the atrial and ventricular windows may be the same or may differ. Moreover, satisfaction criteria and/or lengths of the atrial and ventricular windows may be programmed to change during detection, redetection, and verification procedures. It is noted that the atrial and ventricular detection operations typically run independent of one another.

Returning to FIG. 3A, each detected atrial interval rate is compared to an atrial rate threshold as part of an atrial interval classification process 204. Based on this comparison, the atrial interval rate is classified 204 relative to one or more thresholds. The thresholds are typically rate thresholds. A detected atrial interval rate is classified as being a fast atrial interval if the atrial interval rate exceeds the atrial rate threshold.

When a predetermined number, percentage or ratio of the atrial interval rates within the atrial detection window are classified as being fast atrial intervals 208, 212 (e.g., the predetermined percentage can be a value between 65–95, 70–90, or 75–85 percent of the atrial interval rates, with 80 percent being an acceptable value), the system 20 is "satisfied" that the atrial interval rates for the heart are properly classified according to the predefined classification parameters for the atrial window.

An atrial episode is declared 216 upon satisfaction of the atrial window satisfaction criterion. Subsequent satisfaction/verification processes may be performed to ensure that the atrial episode is a sustained, rather than transitory, atrial episode. If the atrial detection window is not satisfied, the system 20 returns to the atrial detection window and classification processes, which are operative on a continuous basis.

In accordance with one embodiment, the speed at which atrial window detection operations are performed may be increased by use of an atrial pacing inhibiting methodology. An exemplary approach to increasing atrial window detection operations is disclosed in U.S. patent application entitled "Atrial Tachyarrhythmia Detection System and Method," U.S. Patent Application Publication No. 2002/0147472 A1, which is hereby incorporated herein by reference.

With continued reference to FIG. 3A, each detected ventricular interval rate is compared to a ventricular rate threshold as part of the ventricular interval classification process 206. Based on this comparison, the ventricular interval rate is classified 206 relative to one or more thresholds, such as rate thresholds. A detected ventricular interval rate is classified as being a fast ventricular interval if the ventricular interval rate exceeds the ventricular rate threshold.

When a predetermined number, percentage or ratio of the ventricular interval rates within the ventricular detection window are classified as being fast ventricular intervals 210, 214 (e.g., the predetermined percentage can be a value between 65–95, 70–90, or 75–85 percent of the ventricular interval rates, with 80 percent being an acceptable value), the system 20 is "satisfied" that the ventricular rate intervals for the heart are properly classified according to the predefined classification parameters for the ventricular window.

A ventricular episode is declared 218 upon satisfaction of the ventricular window satisfaction criterion. Subsequent satisfaction/verification processes may be performed to ensure that the ventricular episode is a sustained, rather than transitory, ventricular episode. If the ventricular detection window is not satisfied, the system 20 returns to the ventricular detection window and classification processes, which are operative on a continuous basis.

FIG. 3B illustrates various processes associated with ending an atrial episode, such processes being operative after the system 20 declares an atrial episode in a manner discussed above with regard to FIG. 3A. According the embodiment shown in FIG. 3B, and after an atrial episode has been declared 271, atrial events are detected 273 from which atrial interval rates are developed 273. Atrial intervals are classified 275 in the atrial window. If the atrial window remains satisfied 277, as measured against a maintenance satisfaction criterion (e.g., 24 of the last 40 (60%) atrial intervals classified as fast), the system 20 considers the same atrial episode to remain declared 279. The detection and classification processes 273, 275, 277 are repeated.

If the atrial window becomes unsatisfied, such that the maintenance satisfaction criterion is not met, an End of Episode (EoE) duration 281 is initiated. If the atrial window becomes satisfied 283 during the EoE duration, the EoE duration is terminated 285, and the system 20 considers the same atrial episode to remain declared 279. The detection and classification processes 273, 275, 277 are repeated.

If the atrial window remains unsatisfied 283 during and at the expiration 287 of the EoE duration, the system 20 declares 289 the atrial episode to have ended. The system 20 returns to the detection, classification, and windowing processes depicted in FIG. 3A.

Figure 5:
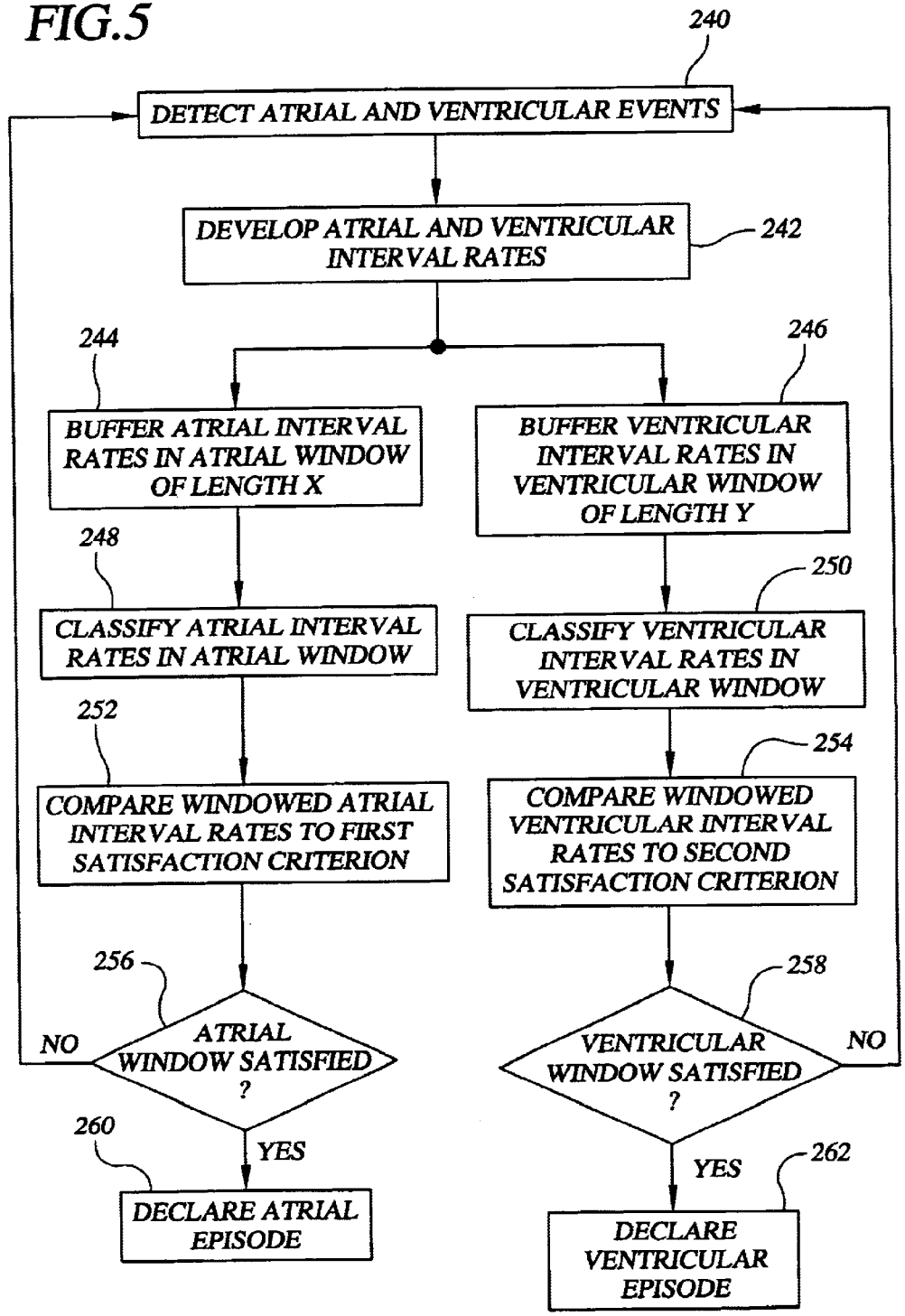
FIG. 5 is a flow chart depicting various processes of an atrial and ventricular arrhythmia detection methodology in accordance with a further embodiment of the present invention.

FIG. 5 is a flow diagram depicting several processes of an arrhythmia detection methodology implemented by system 20 in accordance with another embodiment of the present invention. Atrial and ventricular events are detected 240, from which atrial and ventricular interval rates are developed 242.

Atrial interval rates are buffered 244 in an atrial detection window of length L=X. Ventricular interval rates are buffered 246 in a ventricular detection window of length L=Y, where X and Y are different numbers. The length, X, of the atrial detection window is selected to be greater than the length, Y, of the ventricular detection window to provide for preferential detection and response to ventricular arrhythmias.

The atrial and ventricular interval rates captured within the atrial and ventricular windows are respectively classified 248, 250. The windowed atrial and ventricular interval rates are compared 252, 254 to respective first and second satisfaction criteria. The first and second satisfaction criteria define the basis by which an atrial or ventricular window is satisfied. The first and second satisfaction criteria typically represent a predetermined number, ratio, or percentage of respective atrial and ventricular interval rates captured in an atrial or ventricular window that meet a preestablished threshold.

Comparisons are made to determine if the atrial and ventricular windows are satisfied 256, 258. If not satisfied, the system 20 continues the atrial and/or ventricular event detection and classification processes, which are operative on a continuous basis. If an atrial window is satisfied, an atrial episode is declared 260. If a ventricular window is satisfied, a ventricular episode is declared 262. Additional processes are typically initiated for each of the satisfied windows to determine if the detected atrial or ventricular episodes are sustained, rather than transitory, in nature.

In accordance with another embodiment of the present invention, the system 20 can be programmed to define a number of different rate zones for classifying atrial and ventricular interval rates. The number of atrial and ventricular rate zones typically differ, but may be the same. In one embodiment, for example, ventricular interval rates may be classified using one, two or three ventricular rate zones. Atrial interval rates are typically classified using one or two atrial rate zones.

In general, a number of rate zones are defined to classify atrial and ventricular interval rates that are above a defined upper limit for normal atrial and ventricular interval rates, respectively. A rate zone is a range of atrial or ventricular interval rates that has an associated lower rate threshold. Typically, a given rate zone is defined by its lower rate threshold and that of an adjacent rate zone (e.g., next higher rate zone). For each rate zone, the lower rate threshold is a programmable value in beats per minute (bpm) and is the value to which the system 20 compares each sensed atrial or ventricular interval rate in order to determine the zone in which that atrial or ventricular interval rate belongs.

In one embodiment, ventricular rate zones can be defined for slow ventricular tachycardia (VT-1), fast ventricular tachycardia (VT), and ventricular fibrillation (VF). Atrial rate zones can be defined to classify supraventricular tachycardia (SVT) and atrial fibrillation (AF). The lower rate threshold for each of the atrial and ventricular rate zones may be programmed at a given beat-per-minute as is appropriate.

According to one approach, to determine if an individual atrial or ventricular interval rate falls into a particular programmed rate zone, the system 20 detects the intervals between a series of the most recent consecutive atrial P-waves or ventricular R-waves. Detecting the intervals between 40 of the most recent consecutive atrial P-waves and 10 of the most recent consecutive ventricular R-waves, for example, is considered to be a good sampling.

These atrial and ventricular samplings may be referred to as detection windows, with a new atrial and ventricular detection window occurring with each consecutive atrial P-wave and ventricular R-wave, respectively. The lengths of the atrial and ventricular detection windows, in the above example, are 40 and 10 samples, respectively. The length of the atrial and ventricular windows may be varied, such as between 20–60 and 5–15 samples, for example.

The system assesses the atrial and ventricular intervals in relation to one or more of the predefined atrial and ventricular rate zones, respectively. The use of atrial and ventricular detection windows helps to differentiate and classify atrial and ventricular tachyarrhythmias into a predefined rate zone, and helps to ensure that the correct atrial or ventricular therapy is delivered to the patient.

Figure 4:
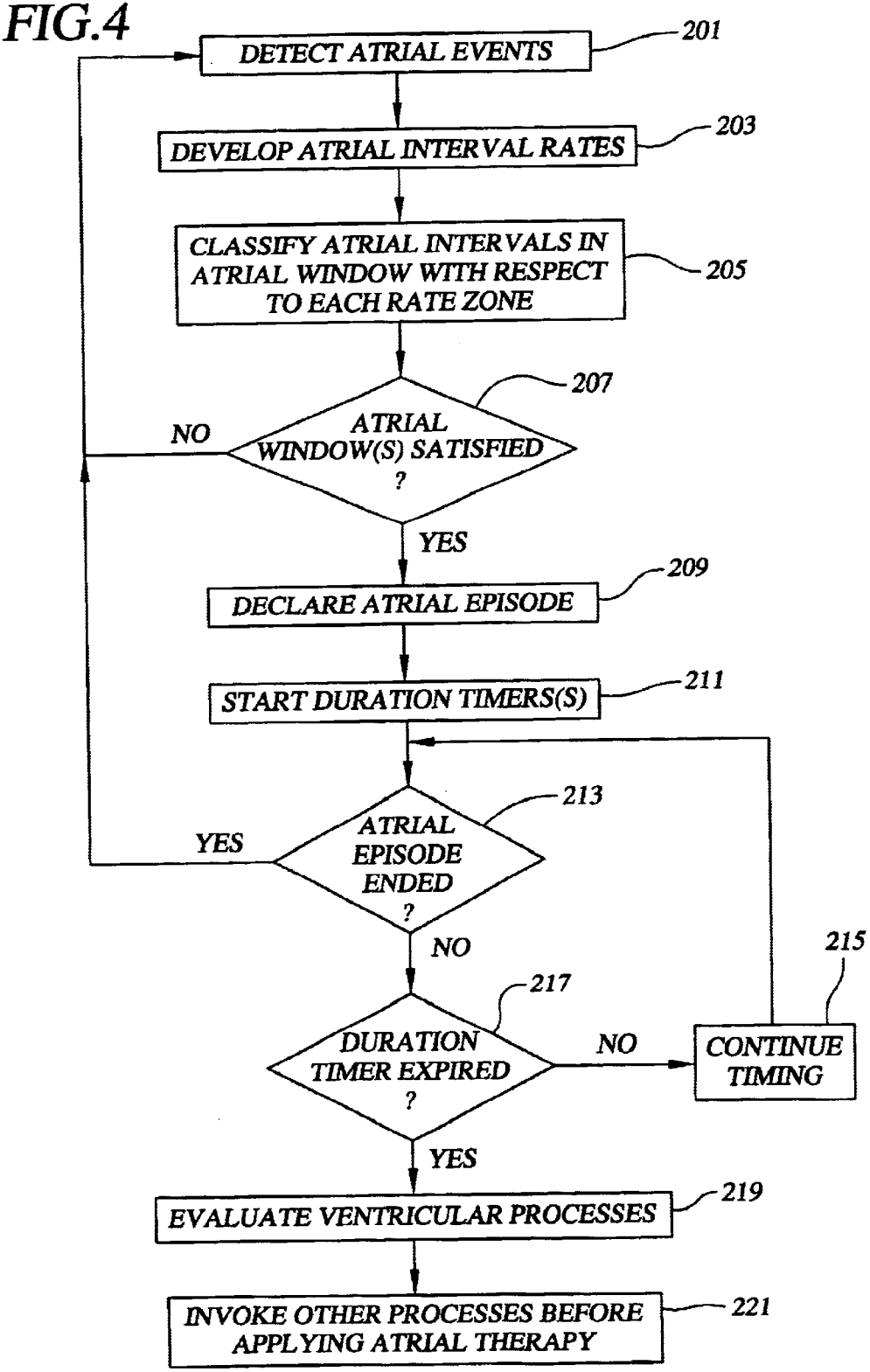
FIG. 4 is a flow chart depicting various processes of an atrial arrhythmia detection methodology in accordance with another embodiment of the present invention.

Turning now to FIG. 4, there is depicted several processes of an atrial arrhythmia detection methodology in accordance with an embodiment of the present invention. In one configuration, each atrial rate zone (e.g., an SVT and an AF rate zone) is associated with a corresponding atrial detection window. According to this embodiment, atrial events are detected 201, from which atrial interval rates are computed 203.

Each detected atrial interval rate is compared to each atrial rate zone's lower rate threshold in the atrial detection window analysis step 205. Based on this comparison, the atrial interval rate is classified 205 as being either a fast or slow interval with respect to each of the atrial rate zones. A slow atrial interval for a given atrial rate zone has an atrial interval rate that is less than that atrial rate zone's lower rate threshold. A fast atrial interval for a given atrial rate zone has an atrial interval rate that is equal to or greater than the atrial rate zone's lower rate threshold.

When 207 a predetermined number, percentage or ratio of the atrial interval rates within an atrial detection window are classified as being fast atrial intervals for a given atrial rate zone, the system 20 is "satisfied" that the atrial interval rates for the heart are properly classified in that atrial rate zone and an atrial episode is declared 209. If the atrial detection window is not satisfied, the system 20 returns to the atrial detection and classification steps 201, 203, 205, which are operative on a continuous basis.

When the system 20 becomes satisfied that the atrial rate intervals for the heart are properly classified in one of the respective atrial rate zones, the system 20 transitions to a cardiac episode condition. If an atrial window becomes satisfied for any of the atrial rate zones (e.g., one or both of two defined atrial rate zones), duration timers are initiated 211. In one embodiment, an ATP (antitachycardia pacing) duration and a Shock duration, which is typically longer than the ATP duration, are concurrently initiated upon satisfaction of an atrial window. A duration time interval defined by a duration timer represents a length of time during which the system 20 continues to monitor and analyze atrial interval rates within an atrial detection window to ensure that the atrial tachyarrhythmia associated with a satisfied rate zone window is sustained, rather than transitory, before the system 20 considers initiating a selected atrial therapy.

In one embodiment, and as discussed briefly hereinabove, two duration timers associated with two atrial durations are concurrently initiated in response to an atrial episode being declared. According to this embodiment, an ATP (antitachycardia pacing) duration timer and a Shock duration timer are initiated concurrently upon declaring an atrial episode by the system 20. The ATP duration may, for example, be programmed to be 30 seconds in duration (ranging from about 10 seconds to 1 hour), and the Shock duration may be programmed to be 1 hour (ranging from about 1 minute to 2 hours).

The system 20 continues to monitor the atrial interval rates within the appropriate shifting detection windows after declaring an atrial episode 209 to determine if an atrial episode has ended 213. Checks are made during these evaluations to determine if at least a maintenance percentage of the atrial interval rates in a given atrial detection window remain classified 213 as fast atrial intervals. The maintenance percentage of the atrial intervals is typically a percentage between 45–75, 55–65, or 55–65 percent of the subsequently captured atrial intervals, where 60 percent is a acceptable value.

If the system 20 determines that an atrial episode has ended 213, the duration timer(s) are terminated and the system 20 continues the previously discussed atrial interval detection, classification, and windowing processes. If the system 20 determines that an atrial episode has not ended at the expiration of a duration timer 215, 217, such as in the manner depicted in FIG. 3B, the system 20 determines 219 whether any ventricular durations are presently active and whether any ventricular therapy is or will be delivered. If such ventricular processes are currently being performed, atrial therapy decisions 221 are delayed until such time as the ventricular decisions have been completed, such as by deciding to withhold or deliver ventricular therapy.

The atrial tachyarrhythmia detection processes described herein may be performed in combination and concurrently with the ventricular tachyarrhythmia detection processes disclosed in commonly owned U.S. Pat. No. 5,978,707, which is hereby incorporated herein by reference.

Figure 7:
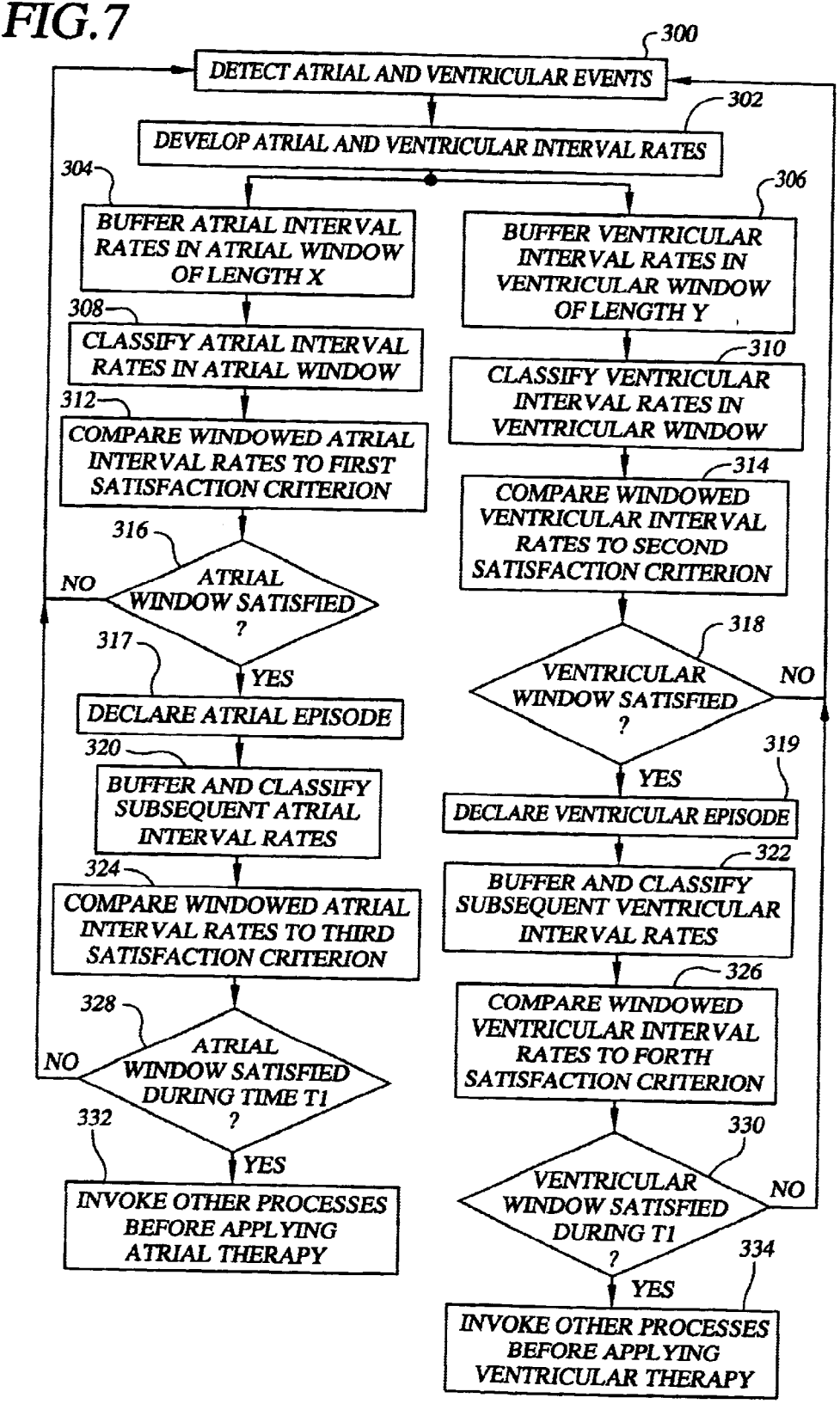
FIG. 7 is a flow chart depicting various processes of an atrial and ventricular arrhythmia detection methodology in accordance with another embodiment of the present invention.

FIG. 7 illustrates several operations associated with an arrhythmia detection methodology according to another embodiment of the present invention. According to this embodiment, atrial and ventricular events are detected 300, from which atrial and ventricular intervals are developed 302. Atrial interval rates are buffered 304 in an atrial detection window of length L=X. Ventricular interval rates are buffered 306 in a ventricular detection window of length L=Y, where X and Y are different numbers. It is understood that the detection and classification operations depicted in FIG. 7 may be performed in connection with a multiple rate zone implementation, but that a single rate zone is assumed in the description of FIG. 7 for purposes of clarity of explanation. Moreover, the use of duration timers is not described in detail in the embodiment of FIG. for purposes of clarity of explanation.

The atrial and ventricular interval rates within the atrial and ventricular windows are respectively classified 308, 310. The windowed atrial and ventricular interval rates are compared 312, 314 to respective first and second satisfaction criteria. According to one configuration, for example, the first satisfaction criterion associated with the atrial window is defined as 32 of the last 40 atrial intervals (80%) classified as fast atrial intervals. The second satisfaction criterion associated with the ventricular window is defined as 8 of the last 10 ventricular intervals (80%) classified as fast ventricular intervals.

Comparisons are made to determine if the atrial and ventricular windows are satisfied 316, 318. If not satisfied, the system 20 continues atrial and/or ventricular event detection and classification processes. If the atrial window is satisfied, an atrial episode is declared 317. If the ventricular window is satisfied, a ventricular episode is declared 319. At this step, one or more duration timers are initiated, as discussed previously.

Subsequent atrial and/or ventricular interval rates are buffered and classified 320, 322 in the respective atrial and ventricular windows. The windowed atrial and ventricular interval rates are compared 324, 326 to respective third and fourth satisfaction criteria. According to one configuration, for example, the third satisfaction criterion associated with the atrial window is defined as 24 of the last 40 atrial intervals (60%) classified as fast atrial intervals. The fourth satisfaction criterion associated with the ventricular window is defined as 6 of the last 10 ventricular intervals (60%) classified as fast ventricular intervals.

If the ventricular window remains satisfied 330 during the verification/re-declaration procedure for a preestablished period of time, such as during a duration time interval T1, other processes are invoked to determine if a ventricular therapy is to be delivered. If the atrial window remains satisfied 328 during the verification/re-declaration procedure for a preestablished period of time, such as during a duration time interval T1, other processes are invoked to determine if an atrial therapy, such as ATP or atrial shock therapy, is to be delivered. As noted previously, one such other process invoked after satisfaction of the atrial window upon elapse of duration time interval T1 involves determining which, if any, ventricular detection processes are presently active so as not to interfere with such processes.

FIG. 8 illustrates several operations associated with an arrhythmia detection methodology according to a further embodiment of the present invention. According to this embodiment, atrial and ventricular events are detected 400, from which atrial and ventricular intervals are developed 402. Atrial and ventricular interval rates are classified 404, 406 in respective atrial and ventricular detection windows. The windowed atrial and ventricular interval rates are compared to applicable satisfaction criteria to determine 408, 410 if the respective atrial and ventricular detection windows are satisfied. If not satisfied, the system 20 continues the atrial and/or ventricular event detection and classification processes.

In general, ventricular tachyarrhythmia detection and therapy is of higher priority than atrial tachyarrhythmia detection and therapy, because ventricular tachyarrhythmia can be life-threatening. As such, the arrhythmia detection algorithm is biased in favor of ventricular tachyarrhythmia detection and therapy. This bias is represented, in part, by differences in atrial and ventricular detection window length, and may further be represented by differences in window satisfaction criteria.

It possible, in certain cases, for both atrial and ventricular tachyarrhythmias to be detected at the same time. For example, atrial fibrillation or atrial flutter can induce a fast ventricular response. Also, a ventricular tachyarrhythmia can, although rarely so, retrograde to cause an atrial tachyarrhythmia to be detected. In order to ensure that ventricular tachyarrhythmia detection and treatment takes precedence over atrial tachyarrhythmia detection and treatment, the processes occurring in response to ventricular window satisfaction take precedence over those occurring in response to atrial window satisfaction.

As is shown in FIG. 8, if the atrial and ventricular windows are both satisfied, priority is given to determining 416 if ventricular therapy is to be initiated, such as by the processes discussed previously. If ventricular therapy is to be initiated, the appropriate ventricular therapy is applied 420. During this time, any atrial therapy that would otherwise have been initiated or is currently in progress is either inhibited or delayed 422 until such time as the ventricular therapy or evaluation process has been completed, which may include subsequent verification that the applied therapy has corrected the ventricular arrhythmia.

If, upon completion of the applied ventricular therapy, the atrial window remains satisfied and atrial therapy is to be initiated 424, other processes are typically invoked to determine the appropriate atrial therapy to be applied 426. Application of the atrial therapy may include subsequent verification that the applied therapy remedied the atrial arrhythmia. Atrial and ventricular event detection and classification is then continued.

In general, and as discussed previously, ventricular arrhythmia detection and therapy delivery is of higher priority than atrial arrhythmia detection and therapy delivery, owing to the life threatening nature of ventricular arrhythmias. An arrhythmia detection approach consistent with the principles of the present invention provides several mechanisms to bias detection and treatment processes toward ventricular arrhythmia detection and treatment.

One such mechanism discussed above involves the use of dual atrial and ventricular detection windows having differing lengths. Another mechanism involves the preference of making ventricular process decisions before atrial process decisions, where both ventricular and atrial detection and therapy decisions are made on the ventricular event (V-sense, V-pace).

According to another mechanism, before a decision is made to attempt atrial therapy, any ventricular durations (i.e., therapy related durations operative following a declared ventricular episode) have to expire. The ventricular detection logic typically evaluates whether to apply or withhold ventricular therapy before atrial therapy is attempted.

Moreover, according to another mechanism, atrial therapy will only be attempted under the condition that the atrial interval rate is greater than the ventricular interval rate for a predetermined number of intervals (i.e., A>V). In other words, atrial therapy will not be attempted for 1:1 rhythms (i.e., the ratio of A rate relative to V rate is 1:1) or if the ventricular rate is faster than the atrial rate. An exemplary approach to implementing this mechanism is disclosed in commonly owned U.S. patent application entitled "Method and Apparatus for Inhibiting Atrial Tachyarrhythmia Therapy," U.S. Patent Application Publication No. 2002/0147474 A1, which is hereby incorporated herein by reference.

With reference to a further mechanism, the nominal settings for atrial durations for atrial therapies are typically much longer than the nominal settings for the ventricular durations. For example, the nominal setting for a ventricular duration may be about 2.5 seconds, in contrast to nominal settings for atrial durations which may range between seconds and 1 hour. An ATP therapy duration, for example, may range between 10 and 60 seconds, with 30 seconds being a suitable duration. An atrial shock therapy duration may, for example, be as long as 1 hour or more.

According to one embodiment, an ATP duration and a Shock duration are initiated concurrently upon declaring an atrial episode by the system 20 (i.e., satisfaction of an atrial window). The atrial ATP duration may be programmed to be 30 seconds in duration, and the atrial Shock duration may be programmed to be 1 hour. At the expiration of the atrial ATP duration, the system 20 determines if any ventricular durations are currently operative (i.e., not expired).

If a ventricular duration is currently active, atrial ATP and atrial shock therapy decisions are delayed until the ventricular duration has expired. If a ventricular duration supercedes or is otherwise initiated during a nominal or initial atrial ATP or atrial shock duration or a re-detect atrial ATP shock duration, which is typically shorter than a nominal or initial atrial ATP duration, the subject atrial ATP or atrial shock duration is reset and the applicable nominal or initial duration is re-initiated.

If all ventricular durations have expired or have never been initiated, additional processes are performed to determine if atrial ATP therapy or other atrial therapy is to be delivered. Such additional processes typically involve one or more of the above-discussed mechanisms. These and other mechanisms may be selectively combined as part of a comprehensive atrial and ventricular arrhythmia detection methodology consistent with the principles of the present invention.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method implemented with an implantable medical device, comprising:
   developing atrial and ventricular interval rates from sensed atrial and ventricular events, respectively;
   classifying atrial interval rates in an atrial window, the atrial window having a first length and a first satisfaction criterion;
   classifying ventricular interval rates in a ventricular window, the ventricular window having a second length and a second satisfaction criterion, the second length of the ventricular window differing from the first length of the atrial window to enhance detection of ventricular arrhythmias relative to atrial arrhythmia detection;
   declaring a ventricular episode in response to satisfying the ventricular window by comparing classified ventricular interval rates to the second satisfaction criterion; and
   declaring an atrial episode in response to satisfying the atrial window by comparing classified atrial interval rates to the first satisfaction criterion.

2. The method of claim 1, wherein the first length of the atrial window is greater than the second length of the ventricular window.

3. The method of claim 1, wherein the first length of the atrial window length is between two times and four times the second length of the ventricular window.

4. The method of claim 1, wherein the first length of the atrial window is at least four times greater than the second length of the ventricular window.

5. The method of claim 1, wherein the first satisfaction criterion is different from the second satisfaction criterion.

6. The method of claim 1, wherein each the first and second satisfaction criterion represents a predetermined number, a predetermined percentage or a predetermined ratio of the classified atrial and ventricular interval rates relative to the first and second lengths.

7. The method of claim 1, wherein the first satisfaction criterion represents a predetermined number, percentage or ratio of the atrial interval rates classified as fast atrial interval rates relative to the first length, and the second satisfaction criterion represents a predetermined number or percentage of the ventricular interval rates classified as fast ventricular interval rates relative to the second length.

8. The method of claim 1, wherein the first satisfaction criterion represents about 80 percent of the atrial interval rates classified as fast atrial interval rates and the second satisfaction criterion represents about 80 percent of the ventricular interval rates classified as fast ventricular interval rates.

9. The method of claim 1, further comprising verifying that the declared atrial episode is a sustained atrial episode in response to the atrial window being satisfied by a third satisfaction criterion for subsequent atrial interval rates.

10. The method of claim 9, wherein each of the first and third satisfaction criterion represents a predetermined number, percentage or ratio of the atrial interval rates classified as fast atrial interval rates relative to the first length, and the third satisfaction criterion is less than the first satisfaction criterion.

11. The method of claim 10, wherein the first satisfaction criterion represents about 80 percent of the atrial interval rates classified as fast atrial interval rates and the third satisfaction criterion represents about 60 percent of the subsequent atrial interval rates classified as fast atrial interval rates.

12. The method of claim 1, further comprising verifying that the declared ventricular episode is a sustained ventricular episode in response to the ventricular window being satisfied by a fourth satisfaction criterion for subsequent ventricular interval rates.

13. The method of claim 12, wherein each of the second and fourth satisfaction criterion represents a predetermined number, percentage or ratio of the ventricular interval rates classified as fast ventricular interval rates relative to the second length, and the fourth satisfaction criterion is less than the second satisfaction criterion.

14. The method of claim 13, wherein the second satisfaction criterion represents about 80 percent of the ventricular interval rates classified as fast ventricular interval rates and the fourth satisfaction criterion represents about 60 percent of the subsequent ventricular interval rates classified as fast ventricular interval rates.

15. The method of claim 1, wherein a plurality of atrial and ventricular windows are operative with respect to each of a plurality of atrial and ventricular rate zones, respectively.

16. The method of claim 15, wherein each of the developing, classifying, and declaring processes are operative with respect to each of the plurality of atrial and ventricular rate zones, respectively.

17. A method implemented with an implantable medical device, comprising:
   developing atrial and ventricular interval rates from sensed atrial and ventricular events, respectively;
   providing an atrial window having a first length and a first satisfaction criterion;
   providing a ventricular window having a second length and a second satisfaction criterion, the second length of the ventricular window differing from the first length of the atrial window to enhance detection of ventricular arrhythmias relative to atrial arrhythmia detection;
   determining if the atrial and ventricular windows are satisfied according to the first and second satisfaction criteria, respectively;
   determining, in response to satisfaction of the ventricular window, whether ventricular arrhythmia therapy is to be initiated; and
   determining whether atrial arrhythmia therapy is to be initiated in response to satisfaction of the atrial window and non-initiation of ventricular arrhythmia therapy.

18. The method of claim 17, further comprising inhibiting or delaying the atrial arrhythmia therapy during a time period in which initiation of ventricular arrhythmia therapy is being determined.

19. The method of claim 17, further comprising inhibiting or delaying the atrial arrhythmia therapy if the atrial and ventricular interval rates are substantially equal.

20. The method of claim 17, further comprising inhibiting or delaying the atrial arrhythmia therapy if an average of the ventricular interval rates is greater than an average of the atrial interval rates.

21. The method of claim 17, further comprising inhibiting or delaying the atrial arrhythmia therapy if an average of the atrial interval rates fails to exceed an average of the ventricular interval rates by at least a predetermined factor.

22. The method of claim 17, further comprising inhibiting or delaying the atrial arrhythmia therapy if a representative atrial rate developed from the atrial interval rates fails to exceed a representative ventricular rate developed from the ventricular interval rates by at least a predetermined factor.

23. The method of claim 22, wherein the representative atrial and ventricular rates represent an average or mean of the atrial and ventricular interval rates, respectively.

24. The method of claim 17, wherein the first length of the atrial window is greater than the second length of the ventricular window.

25. The method of claim 17, wherein the first length of the atrial window length is between two times and four times the second length of the ventricular window.

26. The method of claim 17, wherein the first length of the atrial window is at least four times greater than the second length of the ventricular window.

27. The method of claim 17, wherein each the first and second satisfaction criterion represents a predetermined number, a predetermined percentage or a predetermined ratio of the classified atrial and ventricular interval rates relative to the first and second lengths.

28. The method of claim 17, wherein the first satisfaction criterion represents a predetermined number, percentage or ratio of the atrial interval rates classified as fast atrial interval rates relative to the first length, and the second satisfaction criterion represents a predetermined number or percentage of the ventricular interval rates classified as fast ventricular interval rates relative to the second length.

29. The method of claim 17, further comprising verifying that a declared atrial episode is a sustained atrial episode in response to the atrial window being satisfied by a third satisfaction criterion for subsequent atrial interval rates, each of the first and third satisfaction criterion representing a predetermined number, percentage or ratio of the atrial interval rates classified as fast atrial interval rates relative to the first length, and the third satisfaction criterion is less than the first satisfaction criterion.

30. The method of claim 17, further comprising verifying that a declared ventricular episode is a sustained ventricular episode in response to the ventricular window being satisfied by a fourth satisfaction criterion for subsequent ventricular interval rates, each of the second and fourth satisfaction criterion representing a predetermined number, percentage or ratio of the ventricular interval rates classified as fast ventricular interval rates relative to the second length, and the fourth satisfaction criterion is less than the second satisfaction criterion.

31. The method of claim 17, wherein a plurality of atrial and ventricular windows are operative with respect to each of a plurality of atrial and ventricular rate zones, respectively.

32. The method of claim 31, wherein each of the developing, providing, and determining processes are operative with respect to each of the plurality of atrial and ventricular rate zones, respectively.

33. A body implantable system, comprising:
   at least one lead comprising atrial and ventricular electrodes;
   a detector, coupled to the at least one lead, that senses atrial events and ventricular events;
   memory configured to define an atrial window, having a first length and a first satisfaction criterion, and a ventricular window, having a second length and a second satisfaction criterion, the second length of the ventricular window differing from the first length of the atrial window to enhance detection of ventricular arrhythmias relative to atrial arrhythmia detection; and
   a control circuit coupled to the detector and memory, the control circuit classifying atrial and ventricular interval rates in the atrial and ventricular windows, respectively, declaring a ventricular episode in response to satisfying the ventricular window by comparing classified ventricular interval rates to the second satisfaction criterion, and declaring an atrial episode in response to satisfying the atrial window by comparing classified atrial interval rates to the first satisfaction criterion.

34. The system of claim 33, wherein the control circuit determines whether to initiate ventricular therapy in response to the declared ventricular episode, the control circuit inhibiting or delaying application of atrial arrhythmia therapy during a time period in which initiation of ventricular arrhythmia therapy is being determined.

35. The system of claim 33, wherein the control circuit determines whether to initiate atrial therapy in response to the declared atrial episode, the control circuit inhibiting or delaying the atrial arrhythmia therapy if the atrial and ventricular interval rates are substantially equal.

36. The system of claim 33, wherein the control circuit determines whether to initiate atrial therapy in response to the declared atrial episode, the control circuit inhibiting or delaying the atrial arrhythmia therapy if an average of the ventricular interval rates is greater than an average of the atrial interval rates.

37. The system of claim 33, wherein the control circuit determines whether to initiate atrial therapy in response to the declared atrial episode, the control circuit inhibiting or delaying the atrial therapy if an average of the atrial interval rates fails to exceed an average of the ventricular interval rates by at least a predetermined factor.

38. The system of claim 33, wherein the control circuit determines whether to initiate atrial therapy in response to the declared atrial episode, the control circuit inhibiting or delaying the atrial therapy if a representative atrial rate developed from the atrial interval rates fails to exceed a representative ventricular rate developed from the ventricular interval rates by at least a predetermined factor.

39. The system of claim 38, wherein the representative atrial and ventricular rates represent an average or mean of the atrial and ventricular interval rates, respectively.

40. The system of claim 33, wherein the first length of the atrial window is greater than the second length of the ventricular window.

41. The system of claim 33, wherein the first length of the atrial window length is between two times and four times the second length of the ventricular window.

42. The system of claim 33, wherein the first length of the atrial window is at least four times greater than the second length of the ventricular window.

43. The system of claim 33, wherein each the first and second satisfaction criterion represents a predetermined number, a predetermined percentage or a predetermined ratio of the classified atrial and ventricular interval rates relative to the first and second lengths.

44. The system of claim 33, wherein the first satisfaction criterion represents a predetermined number, percentage or ratio of the atrial interval rates classified as fast atrial interval rates relative to the first length, and the second satisfaction criterion represents a predetermined number or percentage of the ventricular interval rates classified as fast ventricular interval rates relative to the second length.

45. The system of claim 33, wherein the control circuit verifies that the declared atrial episode is a sustained atrial episode in response to the atrial window being satisfied by a third satisfaction criterion for subsequent atrial interval rates, each of the first and third satisfaction criterion representing a predetermined number, percentage or ratio of the atrial interval rates classified as fast atrial interval rates relative to the first length, and the third satisfaction criterion is less than the first satisfaction criterion.

46. The system of claim 33, wherein the control circuit verifies that the declared ventricular episode is a sustained ventricular episode in response to the ventricular window being satisfied by a fourth satisfaction criterion for subsequent ventricular interval rates, each of the second and fourth satisfaction criterion representing a predetermined number, percentage or ratio of the ventricular interval rates classified as fast ventricular interval rates relative to the second length, and the fourth satisfaction criterion is less than the second satisfaction criterion.

47. The system of claim 33, wherein the memory is configured to define a plurality of atrial and ventricular windows operative with respect to each of a plurality of atrial and ventricular rate zones, respectively.

48. The system of claim 47, wherein the control circuit performs the classifying and respective declaring operations with respect to each of the plurality of atrial and ventricular rate zones, respectively.

* * * * *

UNITED STATES PATENT AND TRADEMARK OFFICE
CERTIFICATE OF CORRECTION

PATENT NO. : 6,658,286 B2
DATED : December 2, 2003
INVENTOR(S) : Seim

It is certified that error appears in the above-identified patent and that said Letters Patent is hereby corrected as shown below:

Column 7,
Line 21, "lead is" should read -- lead 24 is --.
Line 24, "heart and" should read -- heart 30 and --.

Column 8,
Line 57, "between and" should read -- between 20 and --.

Column 13,
Line 5, "FIG. for" should read -- FIG. 7 for --.

Column 15,
Line 11, "between" should read -- between 10 --.

Signed and Sealed this

Twentieth Day of April, 2004

JON W. DUDAS
*Acting Director of the United States Patent and Trademark Office*